US007318934B2

(12) United States Patent
Gans

(10) Patent No.: US 7,318,934 B2
(45) Date of Patent: Jan. 15, 2008

(54) METHOD FOR TREATING WOUNDS TO PROMOTE HEALING

(75) Inventor: Arnold M. Gans, Englewood, NJ (US)

(73) Assignee: Medical Nutrition USA, Inc., Englewood, NJ (US)

( * ) Notice: Subject to any disclaimer, the term of this patent is extended or adjusted under 35 U.S.C. 154(b) by 757 days.

(21) Appl. No.: 10/689,236

(22) Filed: Oct. 20, 2003

(65) Prior Publication Data
US 2004/0082502 A1 Apr. 29, 2004

Related U.S. Application Data

(60) Provisional application No. 60/422,164, filed on Oct. 29, 2002.

(51) Int. Cl.
*A61K 9/70* (2006.01)
*A61K 9/48* (2006.01)
*A61K 9/20* (2006.01)

(52) U.S. Cl. .................. 424/443; 424/451; 424/464
(58) Field of Classification Search ................ 424/443
See application file for complete search history.

(56) References Cited

U.S. PATENT DOCUMENTS

| | | | | |
|---|---|---|---|---|
| 4,025,650 | A | * | 5/1977 | Gans et al. |
| 4,042,687 | A | * | 8/1977 | Gans et al. |
| 4,042,688 | A | * | 8/1977 | Gans et al. |
| 4,053,589 | A | * | 10/1977 | Gans et al. |
| 5,733,884 | A | * | 3/1998 | Barbul et al. |
| 5,929,050 | A | | 7/1999 | Petito |
| 5,985,339 | A | * | 11/1999 | Kamarei |

OTHER PUBLICATIONS

Holmgren et al., A hyperstable collagen mimic, Chemistry and Biology, vol. 6, Issue 2, Feb. 1999 pp. 63-70.
Bistrian et al., Nitrogen Metabolism and Insulin Requirements in Obese Diabetic Adults on a Protein-Sparing Modified Fast, Diabetes 1976, 25:494-504.
Breslow et al., The Importance of Dietary Protein in Healing Pressure Ulcers, Journal of the American Geriatrics Society, 1993, 41:357-362.
Evans et al., Pressure Ulcers: Prevention and Management, Mayo Clinic Proceeding 1995, 70:789-799.
Berlowitz et al., Effect of Pressure Ulcers on the Survival of Long-Term Care Residents, The Journals of Gerontology 1997: March, 52(2) M106-110.
Bates, C.J., Proline and hydroxyproline excretion and vitamin C status in elderly human subjects, Clinical Science and Molecular Medicine, 52(5):535-543, 1977.
Ananthanarayanan, V.S., Structural Aspects of Hydroxyproline-Containing Proteins, Journal of Biomolecular Structure & Dynamics, 1(3), 1983, p. 843-855.
Anderson et al., Effects of Dietary Histidine and Arginine on Nitrogen Retention of Men, The Journal of Nutrition, 107:2067-2077, 1977.

Bistrian et al., Effect of a protein-sparing diet and brief fast on nitrogen metabolism in mildly obese subjects, The Journal of Laboratory and Clinical Medicine 1977, 89:1030-1035.
Bistrian et al, Metabolic Aspects of a Protein-Sparing Modified Fast in the Dietary Management of Prader-Willi Obesity, The New England Journal of Medicine 1977, 296:774-779.
Bistrian et al., Protein Status of General Surgical Patients, JAMA 1974, 230:858-860.
Bistrian et al., Effect of mild infectious illness on nitrogen metabolism in patients on a modified fast, The American Journal of Clinical Nutrition 1975, 28:1044-1051.
Blackburn et al., The Effect of Cancer on Nitrogen, Electrolyte and Mineral Metabolism, Cancer Research 1977, 37:2348-2353.
Cherrington et al., Effect of Arginine on Glucose Turnover and Plasma Free Fatty Acids in Normal Dogs, The Journal of the American Diabetes Association, 1973, 22(7) 537-543.
Ferrero et al., Serum Glucagon after Arginine Infusion in Aged and Young Subjects, Journal of the American Geriatrics Society 1980, vol. XXVIII, No. 6, 285-287.
Food Processing, Sweet tasting amino acid, glycine, enhances flavor and provides functional properties, Jul. 1983.
Dingman et al., The penetration of proline and proline derivatives into brain, Journal of Neurochemistry, 1959, vol. 4, 148-153.
Harvey et al., The effects on wound healing of three amino acids—a comparison of two models, British Journal of Dermatology, 1984, vol. 3(27), 171-173.
Lindner et al., Multidisciplinary Approach to Obesity Utilzing Fasting Modified by Protein-Sparing Therapy, Obesity/Bariatric Medicine, 1976, vol. 5(6), 198-216.
Pui et al., Factorial Supplementation with Arginine and Glycine on Nitrogen Retention and Body Weight Gain in the Traumatized Rat, The Journal of Nutrition 1979, 109(2) 240-246.
Pycock et al., The Status of Glycine as a Supraspinal Neurotransmitter, Life Sciences 1981, 28:2679-2686.
Ribaya et al., Effects of Hydroxyproline and Vitamin B-6 on Oxzalate Synthesis in Rats, The Journal of Nutrition 1981, vol. 111(7), 1231-1239.
Sugden et al., Proline and Hepatic Lipogenesis, Biochimica et Biophysica Acta(g) 1984, 798(4), 368-373.
Revis, Jr., MD, Don R., Decubitus Ulcers, www.emedicine.com/med/topic2709.htm.

(Continued)

*Primary Examiner*—Humera N Sheikh
(74) *Attorney, Agent, or Firm*—Lerner, David, Littenberg, Krumholz & Mentlik, LLP

(57) ABSTRACT

A method of treating a mammal to promote wound healing in the mammal in need thereof, comprising orally administering to the mammal an effective amount of a palatable, concentrated protein composition comprising an effective amount of hydrolyzed gelatin and tryptophan, and an ingestible carrier, the composition comprising the essential amino acids required by the mammal. Palatability is preferably achieved by the use of an effective amount of a sweetener. The method is particularly useful for treating wounds resulting from decubitus ulcers and bariatric surgery.

1 Claim, 2 Drawing Sheets

OTHER PUBLICATIONS

European Pressure Ulcer Advisory Panel, Pressure Ulcer Treatment Guidelines, www.epuap.org/glttreatment.html.

Van Der Ven, Cornelly, Biochemical and functional characterisation of casein and whey protein hydrolysates, Jun. 4, 2002.

Strauss et al., Malnutrition in Patients with Pressure Ulcers: Morbidity, Mortality, and Clinically Practical Assessments, Advances in Wound Care 1996:9(5), 37-40.

Thomas, MD, David R., The Role of Nutrition in Prevention and Healing of Pressure Ulcers, Clinics in Geriatric Medicine 1997, vol. 13(3), 497-511.

Ayello et al., Nutritional Aspects of Wound Healing, Wound Care 1999, vol. 17(11), 719-729.

Finucane, MD, Thomas E., Malnutrition, Tube Feeding and Pressure Sores: Data Are Incomplete; American Geriatrics Society 1995, 43:447-451.

* cited by examiner

METHOD FOR TREATING WOUNDS TO PROMOTE HEALING

CROSS-REFERENCE TO RELATED APPLICATIONS

The present application claims the benefit of U.S. Provisional Application No. 60/422,164 filed Oct. 29, 2002, the entire disclosure of which is incorporated herein by reference.

BACKGROUND OF THE INVENTION

The present invention is directed to a method and a composition for treating wounds in a mammal, preferably a person, wherein the composition is taken orally, i.e., ingested, in order to promote healing of such wounds. The composition provides a concentrated and complete source of protein in a palatable form. Consequently, the palatable nature of the composition encourages compliance with a regimen of ingestion by a person in need of such treatment.

In U.S. Pat. No. 4,025,650, and its divisional patents, U.S. Pat. No. 4,042,687, U.S. Pat. No. 4,042,688, and U.S. Pat. No. 4,053,589, A. M. Gans, et al. disclose a method and composition for preventing nutritional deficiency and preventing or treating various medical conditions, including body wastage during oncologic treatment of cancer, obesity, providing rapid body build-up, treatment of nutritional deficiency, particularly that associated with surgery, cardiac cachexia, diabetes, hypoglycemia, gastroenterology, skin conditions related to lipid, cell glycogen and keratin deficiencies, and alcoholism. The disclosure of these patents is incorporated herein by reference to the extent permitted.

Various methods have been proposed for the treatment of wounds; see for example, in U.S. Pat. No. 5,929,050, G. D. Petito, U.S. Pat. No. 5,733,884, A. Barbul et al., and U.S. Pat. No. 5,985,339, A. Kamarei. The disclosures of these patents are incorporated herein by reference to the extent permitted.

A review of the medical journal literature reporting on the relationship between pressure sores or decubitus ulcers and nutrition was undertaken by T. E. Finucane, J. Am. Geriatric Soc., 43(4): 447-51 (1995). Overall, the author of the review concluded that data about the relationship between malnutrition and pressure sores are incomplete and contradictory. Several studies reporting on possible factors that influence pressure wound formation and healing have been reported in the literature including reviews that have carefully considered these reports and tried to analyze their sometimes conflicting conclusions. In general, there is reported a general association between improved nutrition and reduced incidence and improved healing of pressure ulcers. However, the studies rely on the intake of dietary protein requiring digestion, and digestion can be affected by the overall health, well-being and the functionality of critical organs, including the liver and kidneys. In contrast, the supplemental use of enzymatically hydrolyzed collagen, fortified so as to provide all of the essential amino acids, in the form of "pre-digested" protein, has not been considered for its effect on wound healing.

Pressure ulcers are also known as bedsores or decubitus ulcers. The ulcerated area of skin and tissue becomes injured or broken down typically as a consequence of an extended period of uninterrupted pressure or other continuing assault to the skin. Typically, pressure sores develop when the skin and underlying tissue is squeezed between a bone and an external surface, such as a bed or chair. The most common places for pressure ulcers are over bony prominences, such as the elbow, heels, hips, tailbone, ankles, shoulders, back, and the back of the head. Generally, pressure ulcers occur when a person is in a sitting or lying position for too long without shifting his or her weight. Thus, while anyone confined to a chair or bed is at risk, it is more commonly observed in the elderly and infirm. Incontinence and decreased sensory perception, e.g., due to a stroke, also increase the likelihood of developing bedsores. The constant pressure against the skin squeezes the blood vessels that supply nutrients and oxygen to the skin and nearby tissue partially or completely closed, causing a decreased blood supply to the area. The absence or severe reduction of oxygen and nutrients, results in the death of the skin and, potentially, underlying tissues. Left untreated, nearby tissue begins to die, eventually resulting in an ulcer that can also affect the bone. Severe ulceration, i.e., resulting in an opening in the skin can provide an entry for secondary infections; in particularly severe cases decubitus ulcers can result in death.

Several factors have been identified that increase the risk for decubitus ulcers, including: age, elderly people are at higher risk; inability to move certain parts of the body without assistance, such as the result of spinal or brain injury, and neuromuscular disease; malnutrition; being bedridden or in a wheelchair; a chronic condition such as diabetes or an arterial disease that inhibits prevents proper blood flow and nutrition; incontinence resulting in moisture next to the skin for long periods of time causing skin irritation and breakdown; reduced skin strength; and mental disability due to a condition such as Alzheimer's disease, that reduces the ability of an individual to take proper care or seek appropriate treatment when an ulcer forms.

The standard care taken for prevention or treatment include: identifying individuals at high risk for pressure ulcers; frequently changing the position of immobile patients, e.g., at least every two hours to relieve pressure; using items that can help reduce pressure caused by bedsheets and wheelchairs, e.g., pillows, sheepskin, and foam padding, to relieve pressure, and the use of powdered lubricants, salves or skin creams; making sure patients eat healthy, well-balanced meals; encouraging daily exercise, including range-of-motion exercises for immobile patients; following good skin care and personal hygiene.

The National Pressure Ulcer Advisory Panel (NPUAP), and corresponding panels in other countries and regions, e.g., Europe, Australia, etc. provides a rating system for evaluating decubitus ulcers covering a range from Stage I, the earliest signs, to Stage IV, most advanced, as follows:

Stage I: Non-blanchable erythema of intact skin, i.e., a reddened area that does not turn white or lighten when pressed. Discoloration of the skin, warmth, edema, induration or hardness may also be used as indicators, particularly on individuals with darker skin.

Stage II: Partial thickness skin loss involving epidermis, dermis, or both. The ulcer is superficial and presents clinically as an abrasion, blister or shallow crater.

Stage III: Full thickness skin loss involving damage to or necrosis of subcutaneous tissue that may extend down to, but not through underlying fascia. The ulcer presents clinically as a deep crater with or without undermining of adjacent tissue.

Stage IV: Extensive destruction, tissue necrosis, or damage to muscle, bone, or supporting structures with or without full thickness skin loss. Undermining and sinus tracts may also be present.

Guidelines for patient assessment and treatment are also provided, including ensuring adequate dietary intake to prevent malnutrition to the extent that this is compatible with the individual's wishes or condition. A protocol for wound treatment is also summarized and includes the following elements (described in further detail on the European website):

Debridement, which is defined as the removal of devitalized tissue from a wound. Methods of debridement include surgical, enzymatic, autolytic, larvae or a combination.

Cleanse wounds as necessary with tap water or with water suitable for drinking or with saline.

Use a dressing that maintains a moist environment at the wound/dressing interface. Reduce the risk of infection and enhance wound healing by hand washing, wound cleansing and debridement.

Institute, where appropriate, systemic antibiotic therapy for patients with bacteraemia, sepsis, advancing cellulitis or osteomyelitis. Systemic antibiotics are not required for pressure ulcers that exhibit only clinical signs of local infection.

As noted, evaluation of nutritional status is generally considered, as well as a general recommendation such as eating a balanced diet and, if that is not possible, the use of dietary supplements. This is also referred to in an article by D. R. Revis, published at eMedicine.com, wherein it is suggested that dietary supplements, enteral or parenteral feedings may be useful to restore a positive nitrogen balance and a serum protein level of 6 mg per 100 mL or higher to facilitate wound healing.

Bariatric surgery refers to surgical procedures undertaken to relieve morbid obesity, typically defined as being more than 100 pounds above ideal body weight or having a body mass index of greater than 40 kg/m$^2$, in patients unresponsive to non-surgical therapy for weight loss. Such procedures are divided into restrictive and malabsorptive types of operations. The operations most frequently performed include Roux-en-Y gastric bypass, vertical banded gastroplasty, biliopancreatic diversion and its variations, various gastric banding procedures and, in certain circumstances Silastic® ring gastroplasty. These procedures are also performed using minimally invasive and laparoscopic techniques. Naturally, following these surgeries, as with all others, external as well as internal wounds of varying degrees are present. However, bariatric surgery patients are also subject to severely restricted nutritional intake following the surgery. For example, the total daily caloric intake ranges from about 150 to about 300 calories based on three meals each having a volume of less than 2 cooked ounces. Additionally, patients are typically advised to avoid sugar and fat and to eat protein-dense foods. Immediately after surgery only liquids are consumed; subsequently, a combination of liquids and semi-solids is permitted and then, about three weeks after surgery, solid foods are introduced. Consequently, it can be seen that there is a particular need for promoting wound healing in patients undergoing bariatric surgery. The composition of the present invention, having a complete amino acid profile in combination with a high protein concentration and low calorie content, may be particularly suitable for the long-term maintenance of a bariatric patient.

While various protein supplements are commercially available including some with disclosed uses for providing nutritional support to patients with wounds, the need remains for a method of promoting wound healing based on an ingestible composition that provides the proper balance of amino acids and calories in a concentration that does not unduly burden the body with excess fluids and fats.

SUMMARY OF THE INVENTION

A method of treating a mammal to promote wound healing in said mammal in need thereof, comprising orally administering to said mammal an effective amount of a palatable, concentrated protein composition comprising an effective amount of hydrolyzed gelatin and tryptophan, and an ingestible carrier, said composition comprising the essential amino acids required by said mammal. A preferred composition further includes a sweetener, or a flavoring agent or mixtures thereof, in an amount effective to enhance the palatability to the mammal of the composition. An embodiment comprises a method of treating a mammal to promote wound healing in the mammal, e.g., a person, in need thereof, comprising orally administering to the person an effective amount of a composition comprising hydrolyzed gelatin, e.g., about 5 to about 75 parts by weight; tryptophan, e.g., about 0.02 to about 2.0 parts by weight; a sweetener, e.g., about 0.1 to about 2 parts by weight; and an ingestible carrier, e.g., about 5 to about 100 parts by weight. The composition comprises the essential amino acids required by the person. In a preferred embodiment, the composition is in a liquid form, e.g., an aqueous composition, and is administered as a 1 ounce (30 mL) dosage in which there is present 15 grams of enzymatically hydrolyzed protein, a sweetener and flavoring agent. In other embodiments, each dosage has about 64 calories or about 101 calories; selection of the calorie level being made according to the patient's condition and/or the nature or source of the wound being treated.

DETAILED DESCRIPTION

Figure 1:
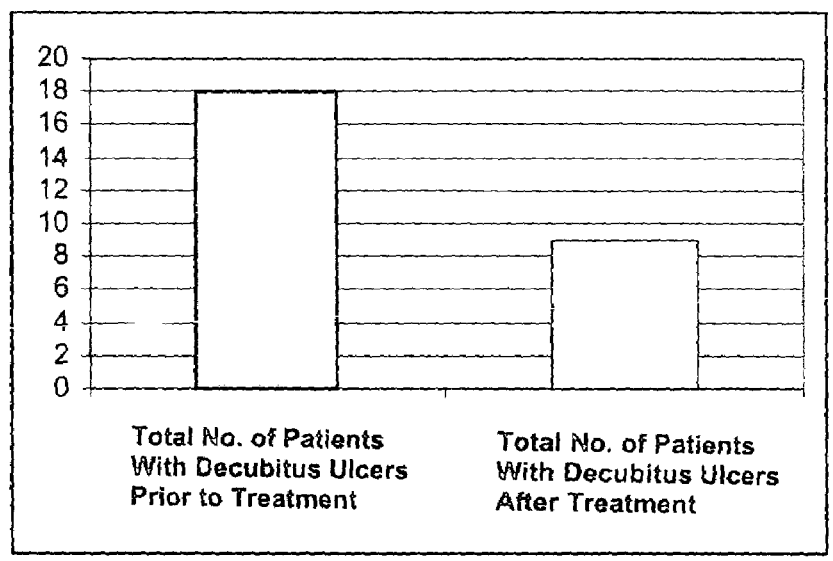
FIG. 1 illustrates the results of a patient study relating to decubitus ulcers using the method of the invention and expressed in terms of number of patients treated and improved.

In its liquid form, the present invention comprises an aqueous composition preferably containing a gelatin hydrolysate, sorbitol, a palatable acid, such as citric acid, fumaric acid or adipic acid, for maintaining an appropriate acid pH, tryptophan, a synthetic sweetener, and flavoring agents when desired. Preferably, one or more preservatives are included for stabilization purposes. Preferably, the flavoring agent is one which is highly palatable and sweet, for example, cherry, orange, green apple, or the like, while the preservative agent may be any of a number of preservatives generally recognized as safe for human consumption, such as potassium sorbate, sodium benzoate, and the methyl-, propyl-, butyl-, and ethylesters of p-hyroxybenzoic acid, the latter esters available under trade names methyl paraben, propyl paraben, etc. The preservatives can be used either alone or in admixture.

The gelatin hydrolysate used for preparing the concentrated protein composition used in the present invention is made by hydrolyzing animal collagen. For example, the animal collagen can be derived from the skin of one or more animals selected from the group consisting of the pig, bovine, ox, cow, calf, bull, sheep, goat, antelope and buffalo. Preferred are the commercially available collagen hydrolysate products derived, for example, from the skin of pork bellies and cattle, e.g. cows, calves, etc., by means of well-known hydrolysis processes to produce a gelatin product. Commercial sources of gelatin can be obtained from various manufacturers including, e.g., Atlantic Gelatin/Kraft Foods, Cangel, Inc., Eastman Gelatine Corp., Gelita North America, PB Leiner and Rousselot, Inc., as well as others worldwide. Although gelatin is soluble in warm water, cooling such a solution results in a gel. In contrast, an aqueous composition of enzymatically hydrolyzed gelatin, used to produce the desired peptides for use in the present invention, does not gel. It is particularly preferred to carry out enzymatic hydrolysis rather than acid or base hydrolysis because the use of an enzyme converts the gelatin to the more palatable small peptides (i.e., mono-, di-, or tri-peptides) rather than to the less palatable amino acids. In addition, enzymatic hydrolysis produces fewer distasteful impurities. For convenience however, compositions are described herein in terms of the amino acids.

The structural breakdown of proteins, for example by enzymatic hydrolysis, is referred to as proteolysis. Similarly, a proteolytic enzyme that weakens or breaks the peptide linkages in proteins is referred to as a protease. Many food grade proteases are available for protein hydrolysis and they can be characterized by their origin, e.g., animal, plant or microbial as well as their mode of action. For example, endoproteases cleave amide bonds within the protein chain and exoproteases remove terminal amino acids from proteins or peptides. Examples of proteases useful for hydrolysis of food proteins and potentially useful herein include the serine proteases trypsin, chymotrypsin, and elastase; and the bacterially sourced *bacillus licheniformis* (commercially available as "Alcalase") and *amyloliquefaciens* (e.g., "Substilsin Novo"). Cysteine proteases from plants include papain, bromelain and ficin. Aspartic proteases from animals include pepsin (from porcine and bovine sources) and chymosin (from calves). Fungal aspartic proteases are considered chymosin-like (from *mucor pusillus* and *miehei* or *endothia parasitica*), aspergillo-peptidase A and newlase (from *rhizopus* sp.). Animal metallo protease such as carboxy peptidase A (from the pancreas) and bacterial metallo proteases such as neutral protease (commercially available as "Neutrase" and "Thermolysin") from *bacillus amyloliquefaciens* and thermoproteolyticus, respectively. Commercial mixtures of proteases are available such as crude papain, which is a mixture of papain, chymopapain, and lysozyme; pancreatin, which is a mixture of trypsin, chymotrypsin, elastase, and carboxypeptidase; "Veron P", "Sumyzyme LP", and "Biozyme A," which are mixtures of serine-, aspartic-, and metalloprotease; and "Pronase," which is a mixture of endo- and exoproteases, active at neutral and alkaline pH. (The compilation of useful food-grade proteases is published in the PhD dissertation by C. van der Ven, entitled Biochemical and functional characterisation of casein and whey protein hydrolysates." Jun. 4, 2002) The preferred enzymes for use in the hydrolysis for the present invention are those generally recognized as safe for human consumption. The enzymes particularly preferred for use in the present invention are bromelain, papain, and ficin, especially papain, although the other enzymes described may possibly be used. Processes for hydrolysis of the protein sources identified above and useful in the present invention are well known to those skilled in that art.

The enzymatically hydrolyzed gelatins based on animal collagen do not contain the essential amino acid tryptophan. Therefore, tryptophan is added to the compositions useful in the present invention in an effective amount, for example from about 0.02 to about 2.0 parts by weight of the composition. Other adjustments in the overall amino acid content as well as for individual amino acid components may also be made as necessary or for special purposes or applications. For example, the individual and overall amount of amino acids used should be such that an effective amount of each is provided even though the hydrolyzed collagen source from which the amino acids is obtained varies, e.g., in moisture content. Additionally, if desired, the composition can include an additional amount of one or more amino acid beyond that naturally present in the hydrolyzed animal collagen. For example, an additional amount of hydrolyzed arginine can be included. The content of each of the amino acids may vary somewhat from batch-to-batch within acceptable values for such a composition. Furthermore, the amino acid profile of a composition suitable for use in the present invention can be varied by as much as ±30% by weight; more typically ±25% by weight; for example, ±20% by weight; provided that, if the amount of any particular amino acid is less than the preferred amount, e.g., as illustrated in Table 2 below, it is at least sufficient so that the composition is suitable to achieve the desired wound healing affect.

Although the gelatin hydrolysate of the present invention has a significantly better taste and odor than other gelatin hydrolyzates, particularly those not produced by enzymatic hydrolysis, it does retain a certain amount of acidity. In the case of other gelatin products, it usually is necessary to add large amounts of sugar to at least partially mask the underlying acrid taste. In such instances, artificial sweeteners, such as sodium saccharin or the like, cannot readily be used because the aftertaste of these artificial sweeteners, when combined with the acrid taste of the gelatin product, would make the product relatively unpalatable. In the present product, however, even though a certain small amount of residual acridity might remain, it is capable of being readily masked by artificial sweeteners, with no serious aftertaste problem, except as may be present in the sweeteners themselves. This, however, can be overcome by the inclusion of sorbitol, which not only tastes sweet itself, but also has a surface coating and lubricating effect thereby facilitating ingestion of the composition. Additionally, the sorbitol coats the taste buds, further masking any possible residual acrid taste. In the present invention the sweetener can be a natural sweetener, an artificial sweetener or mixtures thereof. For example, the artificial sweetener is selected from the group consisting of acesulfame potassium, aspartame, neotame, saccharin, sucralose, alitame, cyclamate and mixtures thereof, and the natural sweetener is selected from the group consisting of tagatose, trehalose, a dihydrochalcone, clycyrrhizin, stevioside, thaumatin, erythritol, hydrogenated starch hydolysates, isomalt, lactitol, maltitol, mannitol, sorbitol, xylitol and mixtures thereof. Preferably, the sweetener is the artificial sweetener sucralose. Finally, a flavor enhancer or flavoring agent also can be included in the composition to improve the palatability of the composition. Consequently, the composition useful in the present invention is made palatable, which is distinctly advantageous in order to encourage compliance by the patient with an administration regimen suitable to promote wound healing. In the above manner, a composition is produced that is a sugarless, lipid-free, and free of carbohydrates that effect rapid rise of blood glucose levels. In this respect, sorbitol, unlike sugar, only slowly affects the blood glucose.

A typical electrolyte composition present in a 30 mL dose of the preferred composition useful in the present invention includes, in milliequivalents, about 2.85 Cl$^-$, 3.18 Na$^+$, 0.30 K$^+$, 0.21 Mg$^{++}$, and, in mg, 12.30 P and 4.20 Cu. If desired, the electrolytes of the composition of the present invention can be adjusted by a skilled practitioner to suit the application.

As noted, the typical dose useful in the present invention is about 15 to about 60 mL of the formulated composition; preferably about 20 to about 40 mL; more preferably from about 25 to about 35 mL; for example, about 30 mL or about 1 ounce. While the dose amount can be adjusted for individual needs, a 30 mL portion has been found to be suitable for the average patient. Such a dose is typically administered about three times daily, although greater or fewer administrations are feasible, depending on individual needs. For example, if the patient is in particular need of protein supplementation prior to the presence of a wound, the skilled physician or dietician can adjust the dosing amount and/or frequency as required. In particular, an elderly or bedridden patient who is not eating sufficient quantities of a well-balanced diet and is particularly susceptible to developing, or has developed decubitus ulcers or pressure sores, can be supplemented with the present composition in order to facilitate healing. Similarly, a patient who is preparing to undergo bariatric surgery can ingest the present composition in anticipation of such surgery in order to facilitate healing of the surgical wounds. Importantly, such a patient, having severe volume restrictions on the amount of food that can be eaten at any one time, can ingest the liquid form of the composition of the present invention and receive the necessary daily requirements of protein in 3 to 4 doses of 30 mL's each, particularly for a typical dose containing about 15 grams of protein and including all of the essential and non-essential amino acids. For patients being treated for decubitus ulcers, the compositions and methods of the present invention are preferably used in combination with the standard care previously used for such condition in order to further improve the rate and/or extent of wound healing.

The caloric value of the composition of the present invention can be adjusted to suit the needs of the individual. For purposes of the present invention, the term "calorie" means kilogram calorie as is commonly the case in connection with foods and beverages. Consequently, a reference herein to 100 calories should be understood to mean 100 kilogram calories or 100 kcal. A useful composition of the present invention can be prepared having about 64 calories in a 30 mL dose. Alternatively, a high calorie additive can be included to boost the caloric value of the composition. Useful additives of this type include sucrose, dextrose, fructose, corn syrup, high fructose corn syrup, etc.; fructose is preferred. For example, fructose can be added to the composition and the calorie level can be increased from 64 calories to about 101 calories in the same 30 mL dose size. In this manner a patient requiring high protein, but reduced calories can be accommodated as well as a patient requiring a higher calorie composition. Furthermore, the use of fructose rather than sucrose can be beneficial to a patient with special dietary restrictions, e.g., as a result of diabetes. If desired, teachings of the present invention provide the guidance for adjusting the calorie level as well as the protein level of the composition to suit the needs of particular classes of patients, while still maintaining an advantageous low dose volume.

The high protein concentration in the composition of the present invention typically includes about 10 to about 30 grams of all essential and non-essential amino acids: the non-essential amino acids alanine, arginine (also considered an essential amino acid for children), aspartic acid, cystine, glutamic acid, glycine, hydroxylysine, hyroxyproline, proline, serine, and tyrosine; and the essential amino acids histidine, isoleucine, leucine, lysine, methionine, phenylalanine, threonine, tryptophan and valine.

As an example, useful dosing regimens for promoting the healing of decubitus ulcers and surgical wounds post surgery, based on a 30 mL dose of the composition of the present invention having about 15 grams of the complete amino acid profile described above and about 64 calories, would be as follows:

| Condition | Method | Frequency |
|---|---|---|
| Decubitus ulcers - Stages I/II | PO or GT | BID |
| Decubitus ulcers - Stages III/IV | PO or GT | TID |
| Surgical Wounds | PO or GT | BID or TID |

Abbreviations:
PO = orally;
GT = by gastrointestinal tube;
BID = twice/day;
TID = three times/day The composition of the present invention is particularly rich in the amino acids arginine, glycine, proline and hydoxyproline. These amino acids, particularly at the higher concentrations found in the present invention, especially facilitate wound healing. While various hypotheses can be put forward in an attempt to explain the result, the interaction of the combination of amino acids at various concentrations is complex. The function of each additional ingredient or amino acid in a system not only depends on the general conditions of the system (e.g., temperature and pH), but also to a significant extent on the presence or absence of other components. This can be understood because each new amino acid functions as a new chemical entity that can react with others in the system. These new reactions can include degradation of vitamins, precipitation of minerals, denaturation and crosslinking of proteins, changes in hydrocolloidal behavior of carbohydrates, phase separations, and changes in nutritional bioavailability. In a living system such as a mammal or the human body, particularly one under stress due to a wound or surgery, the effect of addition of an amino acid mixture is understandably particularly complex. It is sufficient for the patient that the benefit is obtained by practicing the method of the present invention.

Furthermore, depending on the severity of the wound(s), the treatment can be continued for as long as necessary in the opinion of the skilled physician or medical professional. Where the wound is associated with bariatric surgery, the composition of the present invention can be continued beyond surgical wound healing in order to facilitate protein supplementation by means of a low volume composition. This is particularly important where the volume permitted to be ingested by a person who has undergone bariatric surgery is significantly limited, especially in the period immediately following such surgery, e.g., about 2 ounces.

Compositions of the present invention are also useful, for example, their use is indicated where an individual exhibits hypoalbuminemia. In elderly individuals hypoalbuminemia is often associated with malnutrition and such malnutrition is commonly defined as an albumin level of less than 3.2 g/dL and associated weight loss. For an institutionalized patient in particular, a low albumin level is an indication for administration of compositions of the present invention. For example, a dosing recommendation for hypoalbuminemia as indicated by an albumin level of less than 2.8 g/dL is 30 cc by mouth (or gastrointestinal feeding tube) of the composition of the present invention at a frequency of three times per day.

Compositions of the present invention are also useful for maintaining a positive nitrogen balance. Nitrogen balance indicates that the rate of protein synthesis in the body equals that of protein breakdown. It is important to maintain a positive nitrogen balance in the body, in order to preserve muscle tissue-lean body mass. If consumption of protein in one's diet is inadequate, negative nitrogen balance will result. Subsequently, the body breaks down the protein in its own muscle tissues in order to reverse the imbalance. Protein is the body's main source of nitrogen, and when it breaks down, nitrogen is excreted. Measuring the amount of nitrogen excretion reflects how much protein is breaking down. A negative nitrogen balance indicates the wasting away of muscles. It is critical to prevent this, especially during illness.

The Net Protein Utilization (NPU) measure reflects the biological value and digestibility of dietary protein. In other words, it indicates how much of the protein we consume is actually available for use. Compositions useful in the present invention exhibit a particularly high NPU. It is the high concentration of four (4) amino acids, arginine, glycine, proline, and hydroxyproline that is responsible for the high NPU in such compositions. This quality will allow for a more vigorous uptake of dietary protein and spare lean body mass from being degraded.

Compositions useful in the present invention generally can be prepared as described in U.S. Pat. No. 4,025,650, incorporated herein by reference to the extent permitted. Preferably, the compositions are liquid, although pulverulent solid or powdered compositions also can be prepared, the latter useful for further preparing capsules, granules and tablets, as well as in gels, lozenges, candy bars and the like, all as described therein. In general, the compositions comprise the ingredients and range of proportions shown in Table 1:

TABLE 1

| Component | Parts by Wt. (Liquid) |
| --- | --- |
| Hydrolyzed gelatin | 5-75 |
| tryptophan | 0.02-2.0 |
| palatable acid (e.g., citric acid) | 0.3-10 |
| sorbitol (70 wt. %) | 7-25 |
| artificial sweetener (e.g. sucralose) | 0.1-2 |
| preservative(s) | 0.4-1 |
| flavor | 0-0.4 |
| water | 15-80 |

As described above, unlike other food supplement compositions that may be in use, the compositions useful in the present invention advantageously include a high concentration of amino acids in a relatively small volume of liquid. Selection of the amounts of the above ingredients is generally made with the objective of maintaining the substantial solubility of the ingredients in the liquid carrier, e.g., water. This facilitates administration of the composition and compliance by the patient.

Two tablespoonfuls or one ounce, e.g., 30 mL, of a typical gelatin hydrolysate according to the present invention includes the following essential and non-essential amino acids. An example of a suitable approximate composition, providing at least about 15 g of soluble protein hydrolysate per 30 mL is shown in the following table:

TABLE 2

| Amino Acid | g/100 g Protein |
| --- | --- |
| L-Alanine | 8.60 |
| L-Arginine | 7.90 |
| L-Aspartic Acid | 5.90 |
| L-Cystine | 0.07 |
| L-Glutamic Acid | 9.90 |
| Glycine | 23.10 |
| L-Histidine | 0.73 |
| Hydroxylysine | 1.00 |
| L-Hydroxyproline | 6.60 |
| L-Isoleucine | 1.30 |
| L-Leucine | 3.00 |
| L-Lysine | 4.30 |
| L-Methionine | 0.73 |
| L-Phenylalanine | 2.30 |
| L-Proline | 15.20 |
| L-Serine | 6.60 |
| L-Threonine | 2.00 |
| L-Tryptophan | 0.40 |
| L-Tyrosine | 0.70 |
| L-Valine | 2.40 |

EXAMPLE 1

The liquid composition prepared in the manner generally disclosed above, and corresponding the amino acid profile in Table 2, was employed in an observational study at an extended care facility for elderly patients. The study was carried out to assess the therapeutic effect of the composition on the healing process of decubitus ulcers in eighteen patients. The patients were followed for a period diagnosis, decubitus ulcers progress, serum albumin level and body weight. Decubitus ulcers progress information included the following: ulcer site, stage and dimensions (length, width, depth). Use of the composition of the invention was initiated at the direction of a physician, registered dietitian and/or registered nurse based on symptoms such as decubitus ulcers, poor appetite, weight loss and low albumin level. Dosing and method of administration are shown in Table 3 along with patient response.

TABLE 3

Patients with Decubitus Ulcers-Results and Findings

| Patient I.D. | Original Decubitus Ulcer (d/u) Site | Stage | Response Change in condition, stage, or size of d/u | Dose | Comments |
|---|---|---|---|---|---|
| H.A. | Buttocks | I | Healed | BID | Tube feeding |
| H.A. | Back | II | Healed | BID | Albumin 2.1 |
| L.J. | L lower leg | III | Healed | OD | |
| L.J. | Back | II | Healed | OD | |
| W.I. | Sacrum | IV | Stage IV, in size | BID | Desirable wt. |
| W.I. | R lat buttocks | II | Healed | BID | |
| W.I. | R med buttock | II | Healed | BID | |
| W.I. | L Buttocks | II | Healed | BID | |
| S.V. | Sacrum | IV | Stage IV, in size | TID | |
| C.W. | R ear | II | Stage II, in size | BID | |
| M.C. | R heel | III | Stage II, in size | BID | |
| L.A. | Sacrum | II | Stage II, in size | BID | |
| N.B. | Sacrum | I | Healed | OD | |
| M.L. | R foot | II | Healed | BID | |
| M.L. | L foot | II | Healed | BID | |
| M.L. | Sacrum | I | Healed | BID | |
| L.A. | Sacrum | IV | Stage IV, no change | BID | Albumin 1.6 |
| L.A. | L inner heel | II | Stage II, in size | BID | Tube feeding |
| B.S. | Trach | III | Healed | BID | Albumin 1.9 |
| G.M. | Sacrum | III | Stage III, in size | BID | Tube feeding |
| M.M. | Sacrum | II | Healed | OD | |
| S.I. | Sacrum | IV | Stage IV, in size | BID | Tube feeding |
| S.I. | L big toe | II | Healed | BID | |
| S.I. | L hip | IV | Stage IV, much reduced | BID | |
| L.K. | R heel | II | Healed | OD | |
| G.B. | L great toe | II | Healed | BID | Tube feeding |
| F.E. | Sacrum | II | Stage I | OD | Redness |
| F.E. | L scapula | II | Stage II, in size | OD | |
| W.M. | L heel | I | Healed | TID | Tube feeding |
| W.M. | Sacrum | IV | Stage IV, in size | TID | |

Column headed "Dose" refers to frequency of administration; abbreviation "OD" = every day; others defined above.

Figure 2:
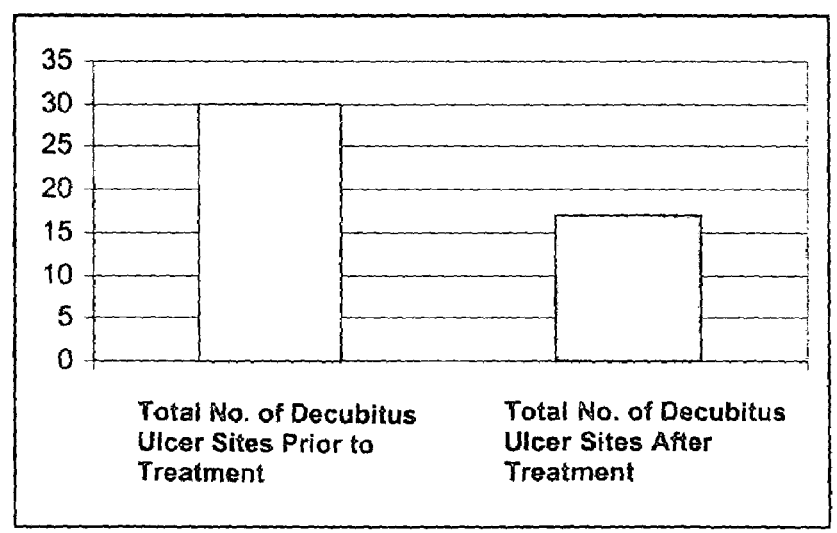
FIG. 2 illustrates the results of the patient study as in FIG. 1 and expressed in terms of the reduction in the number of decubitus ulcer sites.

The results of study are also shown in FIGS. 1 and 2 in the form of bar charts. FIG. 1 shows that, following treatment with the composition of the present invention, there was an overall 50% reduction in the total number of patients with decubitus ulcers. In addition, FIG. 2 shows that 17 of the original total number of decubitus ulcer sites were completely healed following use of the composition of the present invention.

EXAMPLE 2

Figure 3:
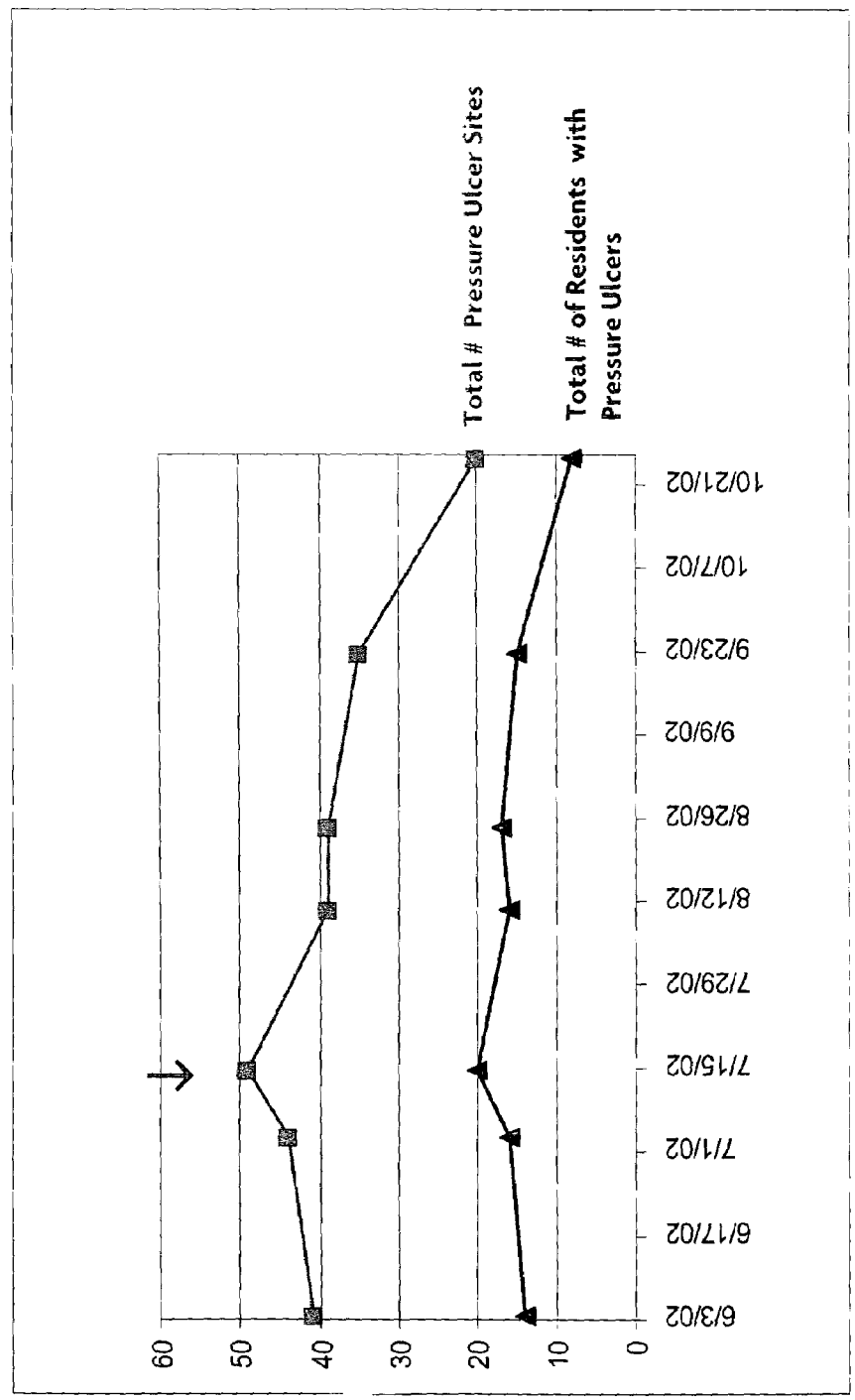
FIG. 3 illustrates the results of a patient study relating to pressure ulcers using the method of the invention and expressed in terms of the total number of residents with pressure ulcers and the total number of pressure ulcer sites as a function of time of treatment.

The liquid composition described above was employed in a study at an extended care facility for elderly patients. The study was carried out to assess the therapeutic effect of the composition on the healing process of decubitus ulcers in residents. The patients were followed for a period of more than four months and the data collected included the following: total number of residents with pressure ulcers and total number of pressure ulcer sites. Patient dosing was at least twice per day and three to four times per day for those patients exhibiting Stage III or Stage IV decubitus ulcers. The results of the study are shown in FIG. 3. The arrow at Jul. 15, 2002 indicates the date on which administration of the composition to residents started; it was continued throughout the time period shown. Overall, there was a 60% reduction in the total number of pressure ulcer sites and a 50% reduction in the number of residents exhibiting pressure ulcers as a result of the administration of the composition of the invention.

The present invention is not only clearly valuable in the treatment of patients exhibiting wounds resulting from decubitus ulcers, but it is similarly valuable for patients undergoing surgery in order to promote wound healing, e.g., particularly in connection with bariatric surgery. In this respect, it may also be used to provide proper nutrition to such patients since the volume of food is severely limited and it is difficult for the patient to consume sufficient nutrition in order to provide adequate protein and/or amino acids. Administration of the composition of the present invention provides such protein, particularly as a consequence of its highly concentrated composition, e.g., 15 g of protein comprising all of the essential and non-essential amino acids in a 1 ounce (30 mL) dose size and in a hydrolyzed form that is especially suitable for such patients. In a limited study, it was observed that, for those patients following the required dietary regimen following bariatric surgery based on the above composition, there was a significant ease of administering the necessary protein requirements even under circumstances where food and fluid intake was severely volumetrically restricted. Furthermore, the rate of wound healing was generally faster and, especially compared to the use of powdered protein supplements, there were fewer side effects and hair loss was minimal for such patients.

Method of treating wounds to promote healing by administering by ingestion to a mammal in need of such treatment a composition comprising hydrolyzed gelatin, tryptophan, a sweetener, and an ingestible carrier, the composition comprising the essential amino acids required by the mammal.

The treatment method is particularly suitable for treating decubitus ulcers and wounds resulting from bariatric surgery.

Any range of numbers recited in the specification, or paragraphs hereinafter, describing various aspects of the invention, such as that representing a particular set of properties, units of measure, conditions, physical states or percentages, is intended literally to incorporate expressly herein by reference or otherwise, any number falling within such range, including any subset of numbers or ranges subsumed within any range so recited. Additionally, the term "about" when used as a modifier for, or in conjunction with, a variable, is intended to convey that the values and ranges disclosed herein are flexible and that practice of the present invention by those skilled in the art using, e.g., temperatures, concentrations, amounts, contents, carbon numbers, properties such as viscosity, particle size, surface area, solubility, etc., that are outside of the stated range or different from a single value, will achieve the desired result, namely, promoting wound healing by the ingestion of a defined composition.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

The invention claimed is:

1. A method of treating a mammal to promote wound healing in said mammal in need thereof, comprising orally administering to said mammal an effective amount of a concentrated protein composition comprising about 5 to about 75 parts by weight of enzymatically hydrolyzed gelatin, about 0.1 to about 2 parts by weight of a sweetener, and about 5 to about 100 parts by weight of an ingestible carrier, said composition comprising the following amino acids, in grams per hundred grams of protein, each numerical value preceded by the word about:

| Amino Acid | g/100 g Protein |
| --- | --- |
| L-Alanine | 8.60 |
| L-Arginine | 7.90 |
| L-Aspartic Acid | 5.90 |
| L-Cystine | 0.07 |
| L-Glutamic Acid | 9.90 |
| Glycine | 23.10 |
| L-Histidine | 0.73 |
| Hydroxylysine | 1.00 |
| L-Hydroxyproline | 6.60 |
| L-Isoleucine | 1.30 |
| L-Leucine | 3.00 |
| L-Lysine | 4.30 |
| L-Methionine | 0.73 |
| L-Phenylalanine | 2.30 |
| L-Proline | 15.20 |
| L-Serine | 6.60 |
| L-Threonine | 2.00 |
| L-Tryptophan | 0.40 |
| L-Tyrosine | 0.70 |
| L-Valine | 2.40. |

* * * * *